United States Patent [19]

Yewer, Jr.

[11] Patent Number: 5,178,163
[45] Date of Patent: Jan. 12, 1993

[54] SUPPORT BELT

[76] Inventor: Edward H. Yewer, Jr., 6251 N. Hwy. 63, Hartland, Wis. 53029

[21] Appl. No.: 815,651

[22] Filed: Dec. 31, 1991

[51] Int. Cl.⁵ .......................... A61F 5/37; A61F 5/00; A63B 71/00; A41F 3/02
[52] U.S. Cl. ..................................... 128/876; 602/19; 2/338
[58] Field of Search .................. 128/876, 78, 878, 879; 2/321, 337, 338, 309, 311, 312; 272/117, 119, 143; 602/19

[56] References Cited

U.S. PATENT DOCUMENTS

| | | | |
|---|---|---|---|
| 2,002,673 | 5/1935 | Mills | 602/59 |
| 2,909,176 | 10/1959 | Ashe | 602/60 |
| 3,209,370 | 10/1965 | Miller | 2/338 |
| 3,544,408 | 12/1970 | Loew | 2/338 |
| 4,469,740 | 9/1984 | Bailly | 428/212 |
| 4,782,535 | 11/1988 | Yewer | 2/338 |
| 5,036,864 | 8/1991 | Yewer | 2/338 |
| 5,038,718 | 8/1991 | Pfleger | 2/338 |
| 5,054,433 | 10/1991 | Pfleger | 2/338 |
| 5,065,773 | 11/1991 | Jackson | 2/338 |

Primary Examiner—Michael A. Brown
Attorney, Agent, or Firm—Quarles & Brady

[57] ABSTRACT

A support belt has an intermediate perforated foam layer with confronting unperforated fabric layers laminated on the inner and outer surfaces of the foam layer. Through-holes in the foam layer are trapezoid shaped and arranged and oriented in a circumferential grid pattern to provide ventilation, perspiration drainage, strength and stiffness. A high strength strap with a buckle encircles the lamination to secure the belt around a user's waist.

7 Claims, 1 Drawing Sheet

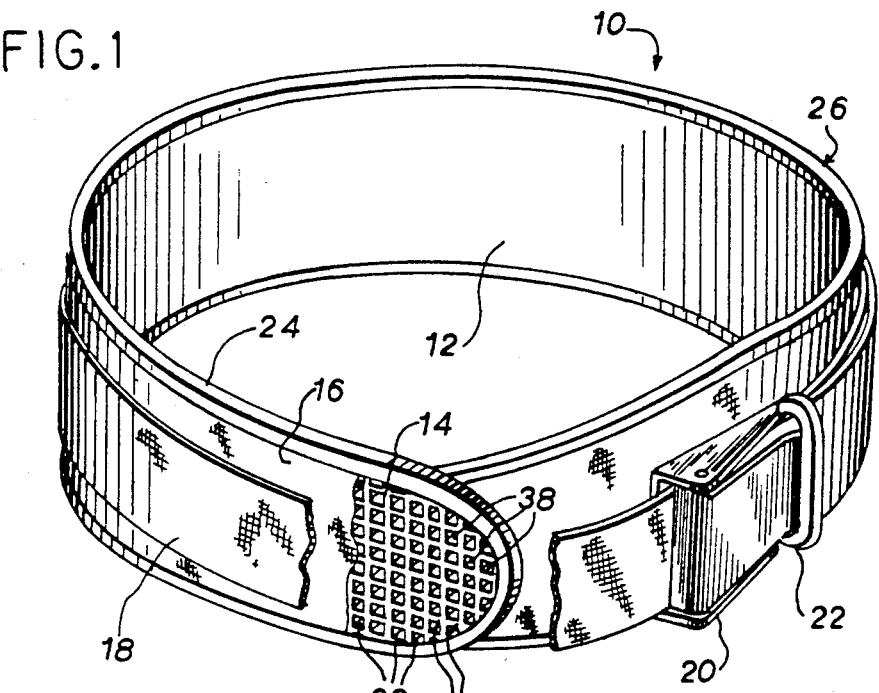
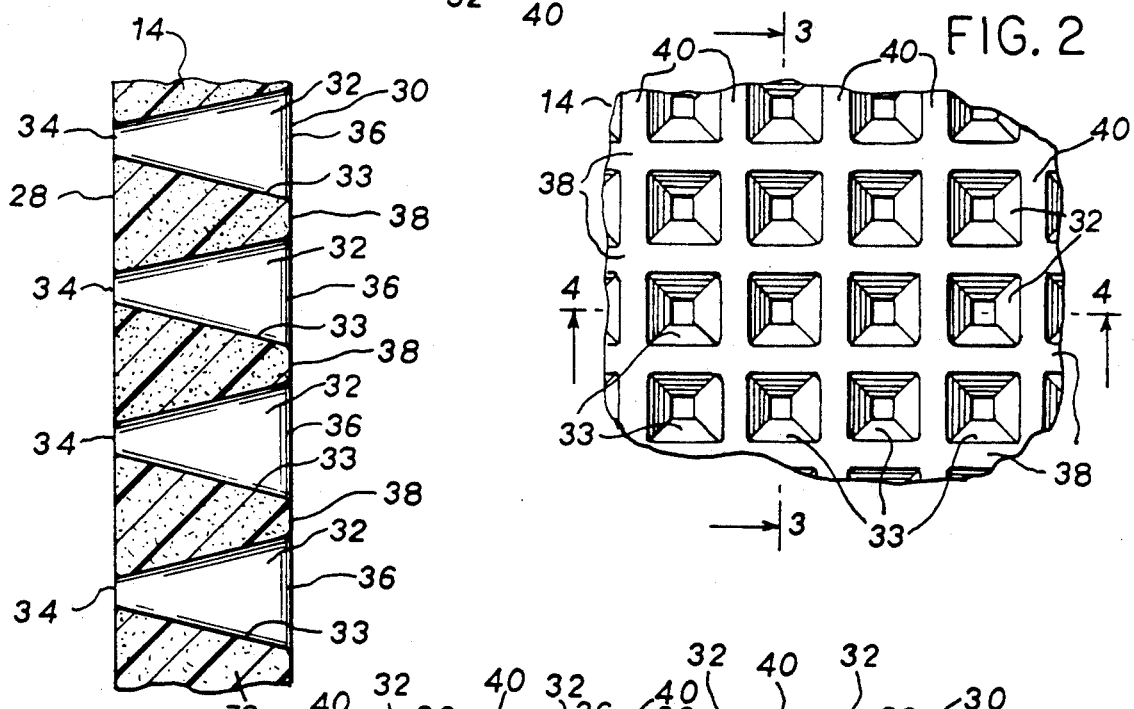
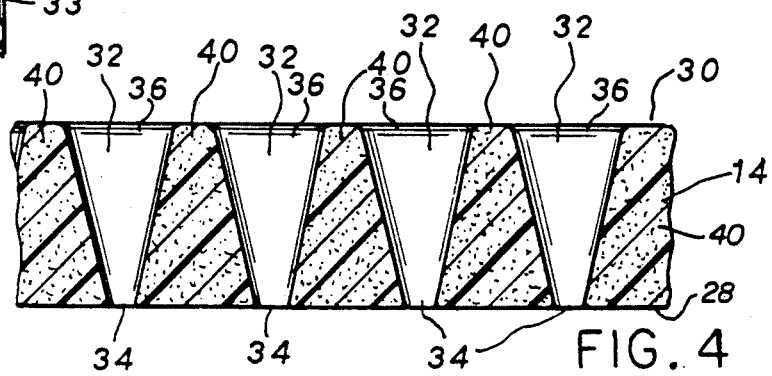

SUPPORT BELT

FIELD OF THE INVENTION

This invention relates to a support belt intended to be secured around the waist of a human user.

BACKGROUND OF THE INVENTION

It is well known that a support belt may be secured around a human user's waist with the effect of increasing the user's strength and load carrying ability, relieving back pain, and other benefits. However, there is a concentration of sweat glands in the abdominal area of the waist where such belts are usually secured which can generate a significant volume of perspiration, and thus that area serves an important purpose for proper cooling of the human body.

Traditionally, support belts have been made of relatively heavy and stiff natural materials, usually leather. An improved belt, made of synthetic materials laminated together is described in U.S. Pat. No. 4,782,535 issued Nov. 8, 1988. In this belt, an inner fabric layer, an intermediate foam layer, and an outer fabric layer are laminated together and a high strength nylon strap is wrapped around the lamination and secured thereto. A buckle is provided to secure the ends of the strap so as to hold the belt around the waist of a user. An improved buckle structure for securing such a belt is described in U.S. Pat. No. 5,036,864, issued Aug. 6, 1991.

Prior belts, while having desirable strength and stiffness characteristics, have in general been made of closed, relatively unbreathable materials. Such belts have not allowed for significant ventilation or perspiration drainage or evaporation of the abdominal area encompassed by the belt and therefore have been hot under some circumstances for the user to wear.

SUMMARY OF THE INVENTION

The invention provides a support belt which is strong and stiff enough to provide the required support to a user but is cooler to wear. The invention is made from a fabric/foam/fabric lamination in which the foam layer is perforated with multiple open through-holes. This construction provides for air exchange between the inner and outer surfaces of the belt and drainage and evaporation of a significant volume of perspiration away from the user's abdominal area.

In a preferred form, the fabric layers are unperforated. It is preferred not to perforate the fabric layers so that the belt is aesthetically pleasing, for easy maintenance and cleaning, and to resist wear and damage to the intermediate foam layer. Moreover, an unperforated inner fabric layer furnishes a larger area of fabric for absorption of perspiration, since the inner fabric layer is normally against or adjacent to the user's waist when the belt is in use, and an unperforated outer fabric layer furnishes a larger area for absorption and evaporation at the outer surface of the belt.

In an especially useful form, the through-holes in the foam layer are arranged in a rectilinear grid pattern having warp ribs and weft ribs orthogonal to the warp ribs. Preferably, the warp ribs are oriented to run for substantially the length of the belt. In this construction, the warp ribs and weft ribs provide substantial circumferential and vertical strength and stiffness while at the same time providing a significant open area for drainage and ventilation.

In another aspect, the through-holes are preferably trapezoidal in shape, with their smaller area ends adjacent to the inner fabric layer and their larger area ends adjacent to the outer fabric layer. A lower surface which is inclined downwardly away from the user's body thereby defines each through-hole, which facilitates the drainage of perspiration away from the body to be drained away or evaporated at the outer surface of the belt.

These and other objects and advantages of the invention will be apparent from the following detailed description and from the drawings.

BRIEF DESCRIPTION OF THE DRAWINGS

FIG. 1 is a perspective view of a belt of the invention shown with a portion of the outer fabric layer broken away so as to reveal an intermediate foam layer;

FIG. 2 is a detail plan view of a portion of the intermediate foam layer shown in FIG. 1;

FIG. 3 is a cross-sectional view taken along the plane of the line 3—3 of FIG. 2; and FIG. 4 is a cross-sectional view taken along the plane of the line 4—4 of FIG. 2.

DETAILED DESCRIPTION OF THE PREFERRED EMBODIMENTS

Referring to FIG. 1, a support belt 10 of the invention is shown. The belt 10 has an inner fabric layer 12, an intermediate foam layer 14, an outer fabric layer 16, a strap 18, a buckle 20 and a torque ring 22. An edge bead 24 is stitched along the edge of the belt 10.

The buckle 20 and torque ring 22 used in the preferred embodiment 10 are disclosed in U.S. Pat. No. 5,036,864, the disclosure of which is hereby incorporated by reference. The fabric layers 12 and 16, the foam layer 14, the bead 24 and the strap 18 may be made of the same materials and laminated and stitched together in the same way as described in U.S. Pat. No. 4,782,535, the disclosure of which is hereby incorporated by reference.

As described in the aforementioned patents, the body 26 of the belt 10 is made by laminating the inner fabric layer 12 on inner surface 28 of foam layer 14, by laminating outer fabric layer 16 on outer surface 30 of the foam layer 14, and by stitching the bead 24 around the edge of the laminated composite structure. Thereafter, the strap 18 is stitched to the body 26 over the outer fabric layer 16 with the buckle 20 secured to one end of the strap 18 and the torque ring 22 held thereon.

The belt 10 differs significantly from the belts described in the aforementioned patents, however, in that the intermediate foam layer 14 is perforated with a rectilinear pattern of open through-holes 32. The through-holes 32 are hexahedrons which are trapezoidal in shape in two dimensions, having smaller area ends 34 opening at inner surface 28 of the foam layer 14 and larger area ends 36 opening at the outer surface 30 of the foam layer 14. It is preferred to position the smaller area ends 34 at the inner surface 28 so that perspiration is drained away from the inner surface 28 by downwardly inclined lower surfaces 33 of the through-holes 32, rather than pooling toward the inner surface 28. Thereby, perspiration can pass from the user's waist through the inner layer 12, be drained toward the outer layer 16 through the intermediate layer 14 by the through-holes 32 without restriction, and be absorbed by and pass through the outer layer 16 to drain away or evaporate. Typically, the foam layer 14 is approximately ¼ inch thick, the ends 34 are approximately 1/12 inches square, the ends 36 are approximately ¼ inches square, and the through-holes 32 are approximately 11/32 inches spaced apart circumferentially and vertically on center.

The through-holes 32 define between them circumferentially extending warp ribs 38 and vertically extending weft ribs 40, the ribs 38 and 40 also being trapezoidal in cross section. The warp ribs 38 extend circumferentially, i.e., longitudinally in the same direction as the strap 18 so that the warp ribs 38 wrap around the waist of a user. For strength and stiffness, the warp ribs 38 are preferably uninterrupted from one end of the belt 10 to the other. The weft ribs 40 are orthogonal to and intersect the warp ribs 38, and preferably extend uninterrupted from the top of the belt to the bottom.

The outer fabric layer 16 is preferably a stretchable or expandable fabric, for example a fabric of about 15% Lycra and 85% nylon has been found suitable. "Lycra" is a trademark of E.I. Dupont de Nemours. An example of a material suitable for the outer fabric layer 16 is woven by Milliken Company and bears catalog no. 5 or S/2539. The inner layer 12 is also preferably made from a stretchable or expandable fabric, for example brushed 100% polyester or nylon. The inner layer 12 may provide a brushed tricot or fuzzy texture, for comfort and improved absorbency of perspiration. The layers 12 and 16 are preferably tightly woven webs to provide a closed weave so that when the fabric is not being stretched, i.e., when it is relaxed, there are no open spaces between the threads in the weave of the fabric. The layers 12 and 16 therefore provide a generally solid, unbroken surface. Although of a closed weave, the layers 12 and 16 are relatively breathable and allow for the passage of air and perspiration through them. The layers 12 and 16 provide these functions even though they are unperforated. As used herein, "unperforated" as applied to the fabric layers 12 and 16 means that the layers 12 and 16 have not been needle punched, die cut or otherwise cut or pierced to have open holes.

The intermediate foam layer 14 is a yieldable foam elastomer having excellent retentive memory characteristics. It is preferred to make the intermediate foam layer 14 of a closed cell polyethylene foam made by Voltech Division of Sekisui American Corporation of Lawrence, Mass. It is preferably a four pound "A" grade ¼ inch thick, 100% polyethylene foam known as "Volara". The foam material of the intermediate layer 14 is radiation cross linked, as opposed to chemical cross linking.

The layers 12, 14 and 16 are laminated together by any suitable method, such as bonding with a suitable flexible adhesive or by a heat combining technique. One acceptable method is known as "Flame Combining" and is supplied under this identifier by United Foam Plastics Corporation of Georgetown, Mass. In this process, a thin (e.g., 0.050 inches thick) urethane foam layer is first applied to each of the fabric layers 12 and 14 on their inside surfaces (the inside surfaces of the fabric layers 12 and 14 are their surfaces which face the foam layer 14) and the composite is passed over a gas flame bar and into pinch rollers, which laminates the urethane foam layers onto the inside surfaces of the fabric layers 12 and 14. Each fabric/urethane foam lamination is then applied on the respective surface (i.e., the lamination of the urethane foam and the layer 12 is placed against surface 28 and the lamination of the urethane foam and the layer 16 is placed against surface 30) with the urethane foam side facing the foam layer 14 and the composite is run over the flame bar and into pinch rollers, for each side. This process is well known in the art as a four pass type in which a first layer is a urethane foam. In the process the urethane foam acts as a bonding agent and any excess largely burns off. In any event, the urethane foam is open cell and therefore breathable, so any remaining would not block air exchange or perspiration drainage between the inner and outer surfaces of the belt 10.

The three laminated layers 12, 14, and 16 have their exposed edges bound by the bead 24, which may be made of any suitable material such as a nylon ribbon, to make the body 26 of the belt 10. The bead 24 is stitched on in any conventional manner preferably using heavy duty nylon thread. Since the foam layer 14 is perforated, the layer 14 may present an interrupted edge at the edge of the belt 10, unless the edge of the foam layer 14 runs along the central portion of a warp rib 38 or a weft rib 40. In any event the bead 24 covers the edge of the layer 14 and, if the edge is interrupted by the through-holes 32, tends to even it out somewhat since the bead 24 is continuous. It is noted that the stitching of the bead 24 is located adjacent to the free edges of the bead 24 and both the inner edge of the bead 24 and the outer edge are stitched in a single pass. The stitching of the bead 24 and of the strap 18 through the foam layer 14 may be interrupted by the through-holes 32, but the frequency and size of the through-holes 32 in the preferred embodiment have been found adequate to firmly secure the bead 24 and strap 18 on the belt 10.

The strap 18 is substantially narrower than the body 26. For example, the strap 18 may typically be approximately 2 inches in width and the body 26 may typically be 4 inches in width, although a wider size may be desirable for applications such as heavy weight lifting usage and a narrower size may be desirable for applications such as aerobics. The strap 18 is a woven fabric of high strength nylon fibers, is sewn to the body 26 of the belt 10 in between the ends of the strap 18 with stitching extending all the way through the body to the inner surface of the inner layer 12, and is provided with the buckle 20 and torque ring 22 on one end and the other end is free. The free end may be provided with a "Velcro" type fastener to secure the free end to the belt 10 after it is threaded through the buckle 20 and torque ring 22.

This construction using a perforated foam layer 14 with unperforated confronting fabric layers has been found to provide improved cooling of a user's abdominal area while still retaining the strength, stiffness and support characteristics which are desirable in a support belt. The foam layer 14 with trapezoidal shaped through-holes arranged in a rectilinear grid pattern is preferred to provide significant open area and perspiration drainage while at the same time the strength and stiffness required in a support belt. Orienting the warp and weft of the foam layer 14 to run circumferentially and vertically provides strength and stiffness in the desired directions and presents edges to which the bead 24 can be secured, even if the edges are interrupted by the through-holes. It is preferred not to perforate the outer fabric layer 12, so that the belt is aesthetically pleasing, for easy maintenance and cleaning, and to resist wear and damage to the foam layer 14. It is preferred not to perforate the inner fabric layer 12 for the foregoing reasons, and also to provide a larger area of fabric for absorption of perspiration, since the inner fabric layer is normally against or adjacent to the user's waist when the belt is in use.

A preferred embodiment of the invention has been described above in considerable detail. Many modifications and variations of the preferred embodiment will be apparent to those of ordinary skill in the art, which will still embody the invention. For example, while the through-holes in the intermediate foam layer are preferably trapezoidal in shape, they could be made conical, cylindrical, rectilinear or some other shape. In addition, while the through-holes in the preferred embodiment are arranged in a rectilinear grid pattern oriented circumferentially, the through-holes could be arranged in some other pattern such as randomly or diagonally and/or could be in some other orientation. Therefore, the invention should not be limited to the preferred embodiment described, but should be defined by the claims that follow.

I claim:

1. A support belt, comprising:
   an inner fabric layer of a closed weave;
   an intermediate foam layer;
   an outer fabric layer of a closed weave;
   wherein said layers are laminated together; and
   adjustable means for encircling a human body for securing said belt around said body;
   wherein said foam layer is perforated with multiple open through-holes; and
   wherein said fabric layers cover said open through-holes on at least one side of said foam layer.

2. A support belt as in claim 1, wherein said fabric layers cover said open through-holes on both sides of said foam layer.

3. A support belt as in claim 1, wherein said through-holes are trapezoidal in shape.

4. A support belt as in claim 3, wherein said through-holes each have a smaller area end and a larger area end, and the smaller area ends of the through-holes are located adjacent to the inner fabric layer and the larger area ends are located adjacent to the outer fabric layer.

5. A support belt as in claim 1, wherein said through-holes are defined in part by a lower surface which is inclined downwardly in the direction from the inner fabric layer to the outer fabric layer.

6. A support belt comprising:
   an inner fabric layer;
   an intermediate foam layer;
   an outer fabric layer;
   wherein said layers are laminated together; and
   adjustable means for securing said belt around a body;
   wherein said foam layer is perforated with multiple open through-holes;
   wherein said fabric layers cover said open through-holes on at least one side of said foam layer;
   wherein the through-holes in said foam layer are arranged in a rectilinear grid pattern, said foam layer having warp ribs and weft ribs orthogonal to said warp ribs.

7. A support belt as in claim 6, wherein said warp ribs are oriented to run for substantially the length of said belt.

* * * * *